United States Patent
Barham

(10) Patent No.: US 10,234,405 B2
(45) Date of Patent: Mar. 19, 2019

(54) STEAM WETNESS MEASUREMENT WITH MICROWAVE TOMOGRAPHY

(71) Applicant: General Electric Company, Schenectady, NY (US)

(72) Inventor: Scott Anthony Barham, Tamworth (GB)

(73) Assignee: General Electric Company, Schenectady, NY (US)

( * ) Notice: Subject to any disclaimer, the term of this patent is extended or adjusted under 35 U.S.C. 154(b) by 256 days.

(21) Appl. No.: 15/358,855

(22) Filed: Nov. 22, 2016

(65) Prior Publication Data

US 2018/0143146 A1    May 24, 2018

(51) Int. Cl.
- G01R 19/00 (2006.01)
- G01N 22/04 (2006.01)
- F01D 17/08 (2006.01)
- F01K 23/10 (2006.01)

(52) U.S. Cl.
CPC ........... *G01N 22/04* (2013.01); *F01D 17/08* (2013.01); *F01K 23/10* (2013.01); *Y02E 20/16* (2013.01)

(58) Field of Classification Search
CPC   G01R 19/0092; G01R 19/0084; G01R 19/00; G01R 19/2513
USPC ....... 324/600, 500, 664, 665, 669–672, 464, 324/465, 122, 514, 76.11
See application file for complete search history.

(56) References Cited

U.S. PATENT DOCUMENTS

| 6,674,054 | B2 * | 1/2004 | Boyers | C03C 23/00 134/102.1 |
| 7,295,933 | B2 * | 11/2007 | Gysling | G01F 1/74 702/100 |
| 8,941,396 | B2 * | 1/2015 | Cok | G01D 5/12 235/492 |
| 2007/0044572 | A1 * | 3/2007 | Davis | G01F 1/66 73/861.42 |

(Continued)

FOREIGN PATENT DOCUMENTS

| CN | 103940851 A | 7/2014 |
| CN | 105716548 A | 6/2016 |

OTHER PUBLICATIONS

Unknown; "Roxas Watercut meter"; Emerson Process Management; Product Data Sheet; Apr. 4, 2016; Copyright 2016 Emerson Electric Co.; pp. 11.

(Continued)

*Primary Examiner* — Jermele M Hollington
*Assistant Examiner* — Taqi R Nasir
(74) *Attorney, Agent, or Firm* — Ernest G. Cusick; Hoffman Warnick LLC

(57) ABSTRACT

A system for measuring steam wetness, including: a plurality of microwave sensors for detecting microwave signals passing through a supply of steam flowing through a cavity; a calibration system for calibrating the plurality of microwave sensors; a film measurement system for measuring a characteristic of a film flowing along an inner surface of the cavity; a system for determining a characteristic of the steam flowing through the cavity based on data provided by the plurality of microwave sensors; and a system for determining a wetness of the steam flowing through the cavity based on the characteristic of the steam flowing through the cavity and the characteristic of the film flowing along the inner surface of the cavity.

18 Claims, 4 Drawing Sheets

(56) References Cited

U.S. PATENT DOCUMENTS

| | | | |
|---|---|---|---|
| 2012/0013354 A1* | 1/2012 | Bowler | G01N 27/226 |
| | | | 324/664 |
| 2014/0125359 A1* | 5/2014 | El-Gamal | G01N 27/223 |
| | | | 324/664 |
| 2015/0253164 A1 | 9/2015 | Kersey | |
| 2016/0025665 A1* | 1/2016 | Hebert | G01N 27/223 |
| | | | 324/664 |
| 2016/0047769 A1* | 2/2016 | Barham | G01N 27/223 |
| | | | 324/664 |

OTHER PUBLICATIONS

Rubinger, C. P. L, et al.; "Building a resonant cavity for the measurement of microwave dielectric permittivity of high loss materials"; ResearchGate; Article in Microwave and Optical Technology Letters; Jul. 2007; vol. 49; No. 7; pp. 1686-1690.

Zhonghe, Han et al.; "Study on a Method of Steam Wetness Measurement based on Microwave Resonant Cavity"; The Ninth International Conference on Electronic Measurement & Instruments; ICEMI'2009; Copyright 2009 IEEE; pp. I-604-I-607.

International Search Report and Written Opinion issued in connection with corresponding PCT Application No. PCT/US2017/059033 dated Feb. 22, 2018.

* cited by examiner

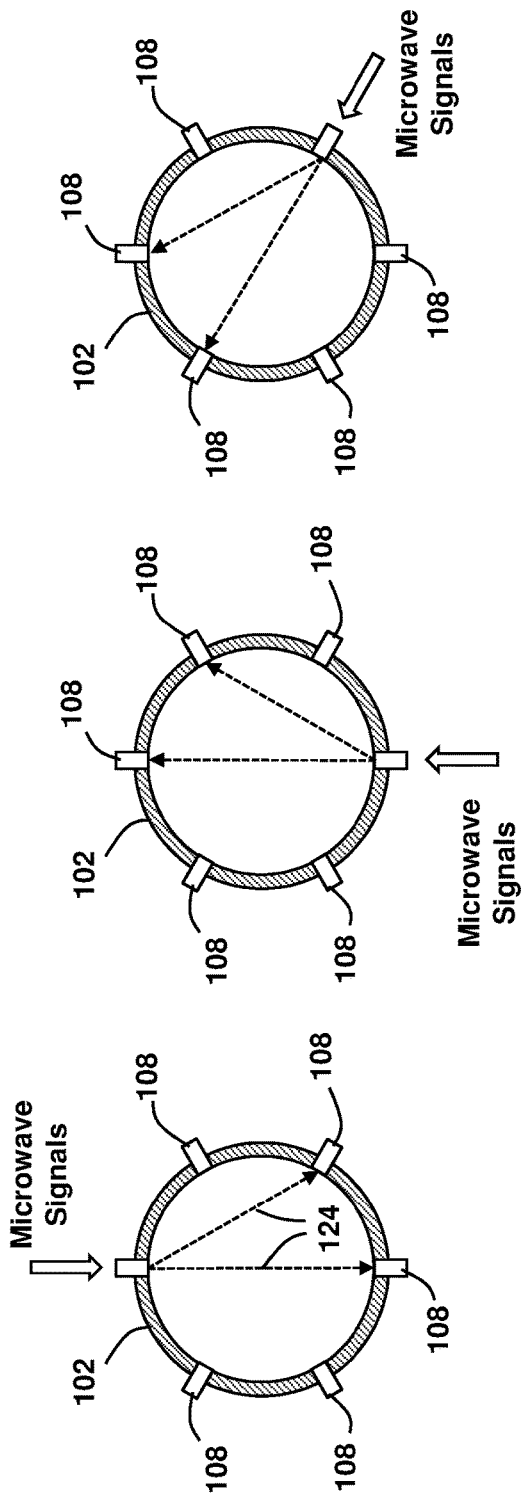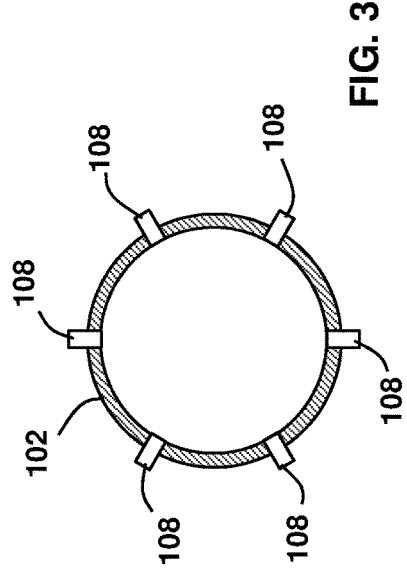

STEAM WETNESS MEASUREMENT WITH MICROWAVE TOMOGRAPHY

BACKGROUND OF THE INVENTION

The disclosure relates generally to the measurement of steam wetness, and more specifically, to the measurement of steam wetness using microwave tomography.

The distribution of water liquid particles in a pipe containing wet steam under flowing conditions is very unpredictable and changes with variations in pipe geometry, direction of flow, temperature, and the like. The water particle and water vapor phases flow at different flow velocities. Also, in some conditions, a thin film of liquid water may flow along the interior surfaces of the pipe in combination with other flow forms. These varying and unpredictable flow phenomena present a formidable measurement problem.

In power plants utilizing steam, it may be advantageous to continually measure the wetness of various steam flows to enable control of steam quality. Steam wetness measurements may be used, for example, to improve process efficiencies and minimize component erosion. Although there are a number of sensor technologies (e.g., microwave-based) that may be used to measure the wetness of steam, such sensors are not capable of providing accurate, real-time steam wetness measurements in high pressure environments (e.g., 70 bar steam flowing through a pipe).

BRIEF DESCRIPTION OF THE INVENTION

A first aspect of the disclosure provides a system for measuring steam wetness, including: a plurality of microwave sensors for detecting microwave signals passing through a supply of steam flowing through a cavity; a calibration system for calibrating the plurality of microwave sensors; a film measurement system for measuring a characteristic of a film flowing along an inner surface of the cavity; a system for determining a characteristic of the steam flowing through the cavity based on data provided by the plurality of microwave sensors; and a system for determining a wetness of the steam flowing through the cavity based on the characteristic of the steam flowing through the cavity and the characteristic of the film flowing along the inner surface of the cavity.

A second aspect of the disclosure provides a method for measuring steam wetness, including: detecting, using a plurality of microwave sensors, microwave signals passing through a supply of steam flowing through a pipe; measuring a characteristic of a film flowing along an inner surface of the pipe; determining a characteristic of the steam flowing through the pipe based on data provided by the plurality of microwave sensors; and determining a wetness of the steam flowing through the pipe based on the characteristic of the steam flowing through the pipe and the characteristic of the film on the inner surface of the pipe.

A third aspect of the disclosure provides combined cycle power generation system, comprising: a gas turbine system; a steam turbine system powered by steam generated using exhaust gases from the gas turbine system; and a system for measuring a wetness of the steam, including: a plurality of microwave sensors for detecting microwave signals passing through a supply of steam flowing through a pipe; a calibration system for calibrating the plurality of microwave sensors; a film measurement system for measuring a characteristic of a film flowing along inner surface of the pipe; a system for determining a characteristic of the steam flowing through the pipe based on data provided by the plurality of microwave sensors; and a system for determining a wetness of the steam flowing through the pipe based on the characteristic of the steam flowing through the pipe and the characteristic of the film flowing along the inner surface of the pipe.

The illustrative aspects of the present disclosure solve the problems herein described and/or other problems not discussed.

BRIEF DESCRIPTION OF THE DRAWINGS

These and other features of this disclosure will be more readily understood from the following detailed description of the various aspects of the disclosure taken in conjunction with the accompanying drawings that depict various embodiments of the disclosure.

FIG. 3 is a cross-sectional view taken along line A-A of FIG. 2 according to various embodiments.

FIGS. 4A, 4B, and 4C depict examples of measurement paths of microwave signals during a phase shift calibration process according to various embodiments.

Figure 1:
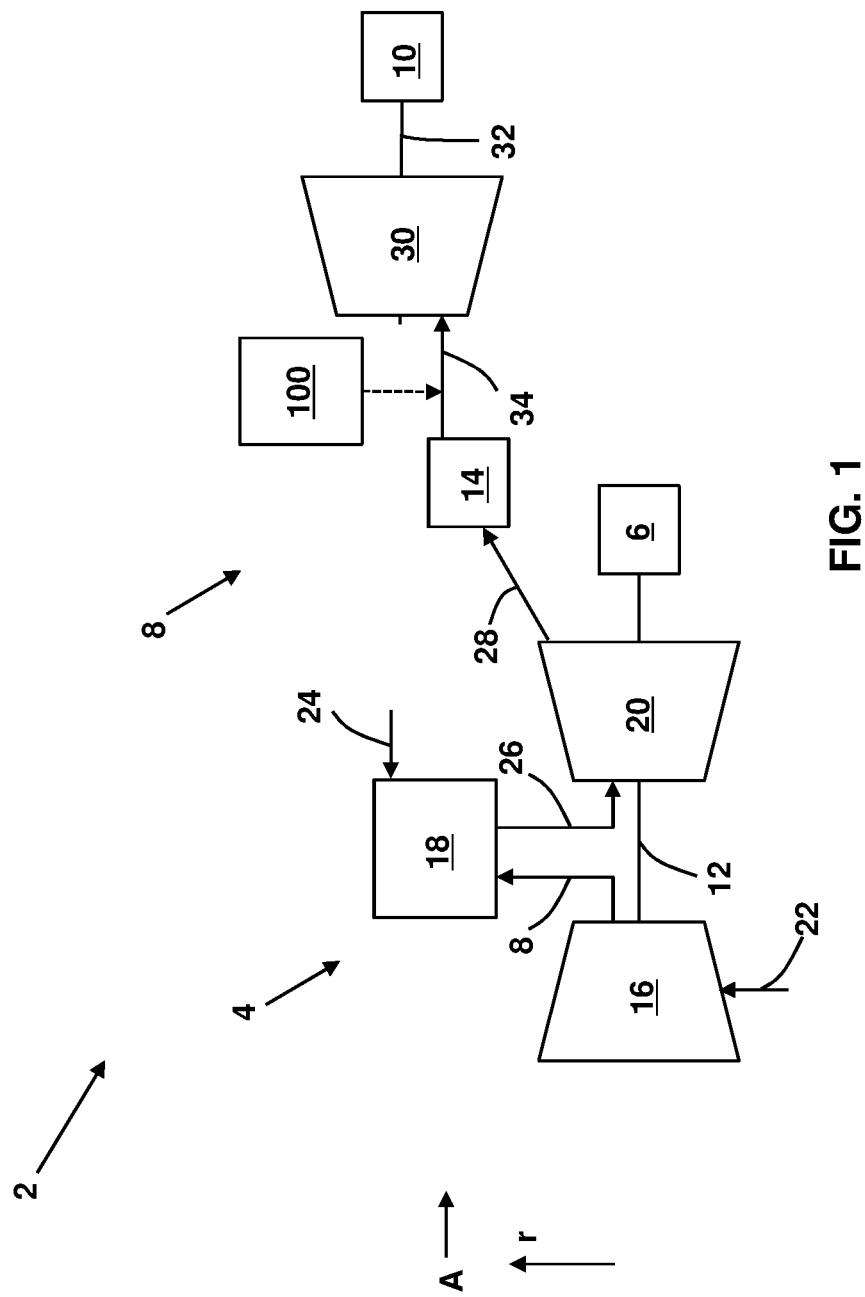
FIG. 1 is a schematic diagram of a combined cycle power generating system according to various embodiments.

It is noted that the drawings of the disclosure are not necessarily to scale. The drawings are intended to depict only typical aspects of the disclosure, and therefore should not be considered as limiting the scope of the disclosure. In the drawings, like numbering represents like elements between the drawings.

DETAILED DESCRIPTION OF THE INVENTION

As indicated above, the disclosure relates generally to the measurement of steam wetness, and more specifically, to the measurement of steam wetness using microwave tomography.

Steam is used in many industrial applications such as heating and power conversion. Under some circumstances, steam includes a water vapor phase, which is gaseous water, and a liquid water phase in which small droplets of water are suspended in the water vapor phase. The amount of liquid water phase relative to the water vapor phase is also called the "wetness factor" or "steam quality" and affects performance of steam in some applications.

Steam quality affects the performance of turbine blades in steam turbine generators. The thermodynamic and aerodynamic performance of turbine blades is determined in part by the surface finish and shape of the blades, which can be affected by steam quality. A steam turbine operating in wet steam conditions has lower thermodynamic efficiency then when operating in dry steam. According to "Baumann's Rule," an increase in steam wetness decreases turbine efficiency. Water droplets from the liquid water phase of steam impact the surface of turbine blades at a high velocity and may corrode the blades. Corrosion of turbine blades may result in thermodynamic and aerodynamic losses in turbine operation and reduces power output of the steam turbine generator. To this extent, it may be advantageous to continually measure the wetness of various steam flows to enable control of steam quality.

Figure 2:
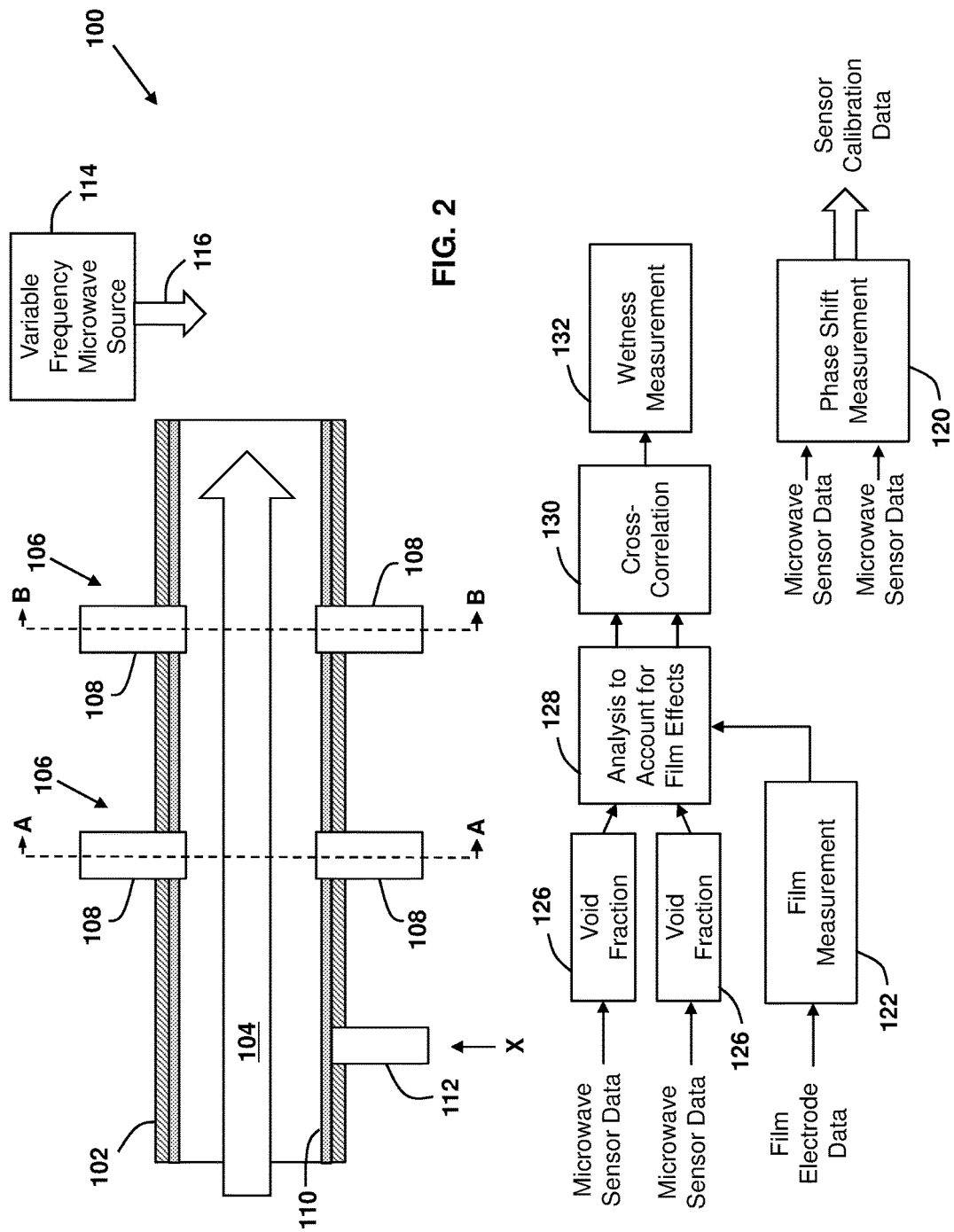
FIG. 2 is a microwave tomography steam wetness measurement system according to various embodiments.

According to embodiments, there is provided a system and method for providing accurate, real-time steam wetness measurements in high pressure environments (e.g., 70 bar steam flowing through a pipe). An example of a steam wetness measurement system 100 according to embodiments is depicted in FIG. 2. In general, the steam wetness measurement system 100 evaluates wet steam by combining multiple measurements obtained using a plurality of high speed microwave transducers, self-calibrated using phase shift measurements, in combination with film measurements.

Turning to FIG. 1, a schematic view of portions of an illustrative combined cycle power generating system 2 is shown. The combined cycle power generating system 2 includes a gas turbine system 4 operably connected to a generator 6, and a steam turbine system 8 operably coupled to another generator 10. The generator 6 and the gas turbine system 4 may be mechanically coupled by a shaft 12. Also shown in FIG. 1, a heat exchanger 14 is operably connected to the gas turbine system 4 and the steam turbine system 8. The heat exchanger 14 may be fluidly connected to both the gas turbine system 4 and the steam turbine system 8 via conventional conduits (numbering omitted).

The gas turbine system 4 includes a compressor system 16 and a combustor system 18. The gas turbine system 4 also includes a gas turbine 20 coupled to the shaft 12. In operation, air 22 enters an inlet of the compressor system 16, is compressed, and then discharged to the combustor system 18 where a supply of fuel 24 is burned to provide high energy combustion gases 26, which drive the gas turbine 20. Typically, the combustor system 18 includes a plurality of fuel nozzles for injecting fuel into a combustion area of the combustor section 18. In the gas turbine 20, the energy of the hot gases is converted into work, some of which is used to drive the compressor system 16 through the rotating shaft 12, with the remainder available for useful work to drive a load such as the generator 6 via the shaft 12 for producing electricity.

FIG. 1 also represents the combined cycle in a simplest form in which the energy in the exhaust gases 28 exiting the gas turbine 20 are converted into additional useful work. The exhaust gases 28 enter the heat exchanger 14 in which water is converted to steam 34. The steam turbine system 8 may include one or more steam turbines 30 (only one is shown), e.g., a high pressure (HP) turbine, an intermediate pressure (IP) turbine, and a low pressure (LP) turbine, each of which are coupled to a shaft 32. The steam turbine 30 includes a plurality of rotating blades (not shown) mechanically coupled to the shaft 32. In operation, steam 34 from the heat exchanger 14 enters an inlet of the steam turbine 30 and is channeled to impart a force on the blades of the steam turbine 30 causing the shaft 32 to rotate. The rotating shaft 32 may be coupled to the generator 10 to produce additional electric power.

Referring now to FIG. 2, there is shown a microwave tomography steam wetness measurement system 100 according to embodiments for measuring the wetness of steam 104 (e.g., steam 34, FIG. 1) passing through a pipe 102. The pipe 102 may include any hollow structure capable of conveying a supply of wet steam 104. Wetness measurements of the steam 104 are performed at at least two different cross-sections (e.g., cross-sections A-A and B-B in FIG. 2) along the pipe 102 using a plurality of sets 106 of microwave sensors 108. The microwave sensors 108 in each set 106 are distributed (e.g., equidistant) about the circumference of the pipe 102. The microwave sensors 108 can be flush to the pipe or extend into the interior of the pipe 102 beyond, and isolated from, the thin film 110 of liquid water flowing along the interior surfaces of the pipe 102. Film measurements (e.g., thickness, film velocity) of the film 110 are performed at at least one location (e.g., location X in FIG. 2) using a set of electrodes 112 to determine the thickness of the film 110 and, over time, the flow velocity of the film 110. Microwaves are generated by a variable frequency microwave source 114, and are routed into the pipe 102 via a waveguide 116.

Microwave sensors 108 are capable of monitoring the wetness of the steam 104 in real time. However, for accurate measurement microwave sensors 108 require calibration and cannot determine the effects of the film 110 on measured data. To obviate these issues, according to embodiments, the microwave tomography steam wetness measurement system 100 includes a microwave phase shift measurement device 120 for self-calibrating the microwave sensors 108, and a film measurement system 122 for determining, using data from the set of electrodes 112, the thickness and flow velocity of the film 110.

It is not possible to use microwave phase shift measurements to determine the effects of the film 110 on steam wetness measurements. Microwave phase shift measurements are also too slow for inline steam wetness measurements, as such measurements involve scanning over a range of frequencies to determine the lowest destructive frequency. However, according to embodiments, microwave phase shift measurements may be used to self-calibrate the microwave sensors 108.

A cross-sectional view taken along line A-A of FIG. 2 is shown in FIG. 3. According to embodiments, a plurality of microwave sensors 108 are arranged about the circumference of the pipe 102.

Microwave phase shift measurements use two separate microwave signals travelling different lengths, within the steam 104, to determine the frequency for a phase change of π. A phase change equal to π will cause destructive interference as the signals will be equal and opposite. The frequency is changed until a frequency is found where the phase change is constant.

Examples of measurement paths of microwave signals 124 to the microwave sensors 108 depicted in FIG. 3 are shown in FIGS. 4A, 4B, and 4C. Multiple phase shift and attenuation measurements across the pipe 102 are taken individually in sequence. Multiple independent phase shift and attenuation measurements are possible for the six sensor system shown in FIG. 3, with three of them shown in FIGS. 4A, 4B, and 4C. The electrical permittivity of the steam 104 can be found in a known manner by determining the lowest frequency at which destructive interference occurs. Calibration of the microwave sensors 108 uses phase shift and attenuation measurements taken at a range of steam 104 wetness to develop a prediction curve; with future phase shift and attenuation measurements fitted to this curve to determine the wetness of the steam 104.

After calibration, wetness measurements of the steam 104 are performed at at least two different cross-sections (e.g., cross-sections A-A and B-B in FIG. 2) along the pipe 102 using a plurality of sets 106 of microwave sensors 108. According to embodiments, the microwave sensors 108 are microwave transducers. Microwave signals of at least one frequency are directed through the steam 104 in the pipe and are detected by the microwave sensors 108. A void fraction analysis 126 is performed in a known manner on the data obtained by the microwave sensors 108 to determine the void fraction of the steam 104 at each cross-section A-A and B-B within the pipe 102. The void fraction, which is an indicator of the quality of the steam 104, is the volume $V_g$ occupied by the gas phase of the steam 104 relative to the volume $V_{steam}$ of the steam 104:

$$\text{Void Fraction} = V_g/V_{steam}$$

The film measurement system 122 receives electrical conductivity data of the film 110 from the set of electrodes 112. The electrical conductivity data may include, for example, the capacitance or resistance of the film 110, dependent on the type of conductivity measured. The film measurement system 122 calculates the thickness of the film 110 in a known manner. Analysis of the film thickness over time at one or more locations along the pipe 102 may be used to determine the velocity of the film 110 flowing through the pipe 102.

The film measurement data (film thickness and flow velocity of the film 110) provided by the film measurement system 122 and void fraction data provided by the void fraction analysis are then analyzed 128 to account for the effect of the film 110 on the void fraction data provided by the void fraction analysis 126. Based on the analysis 128, adjustments may be made to the components of the microwave tomography steam wetness measurement system 100 and/or the void fraction data to increase the accuracy of the steam wetness measurement. This allows a more accurate separation of measurement data associated with the film 110 and the steam 104. The resultant data at each cross-section A-A and B-B within the pipe 102 is cross-correlated 130 to determine a steam wetness measurement 132.

Figure 5:
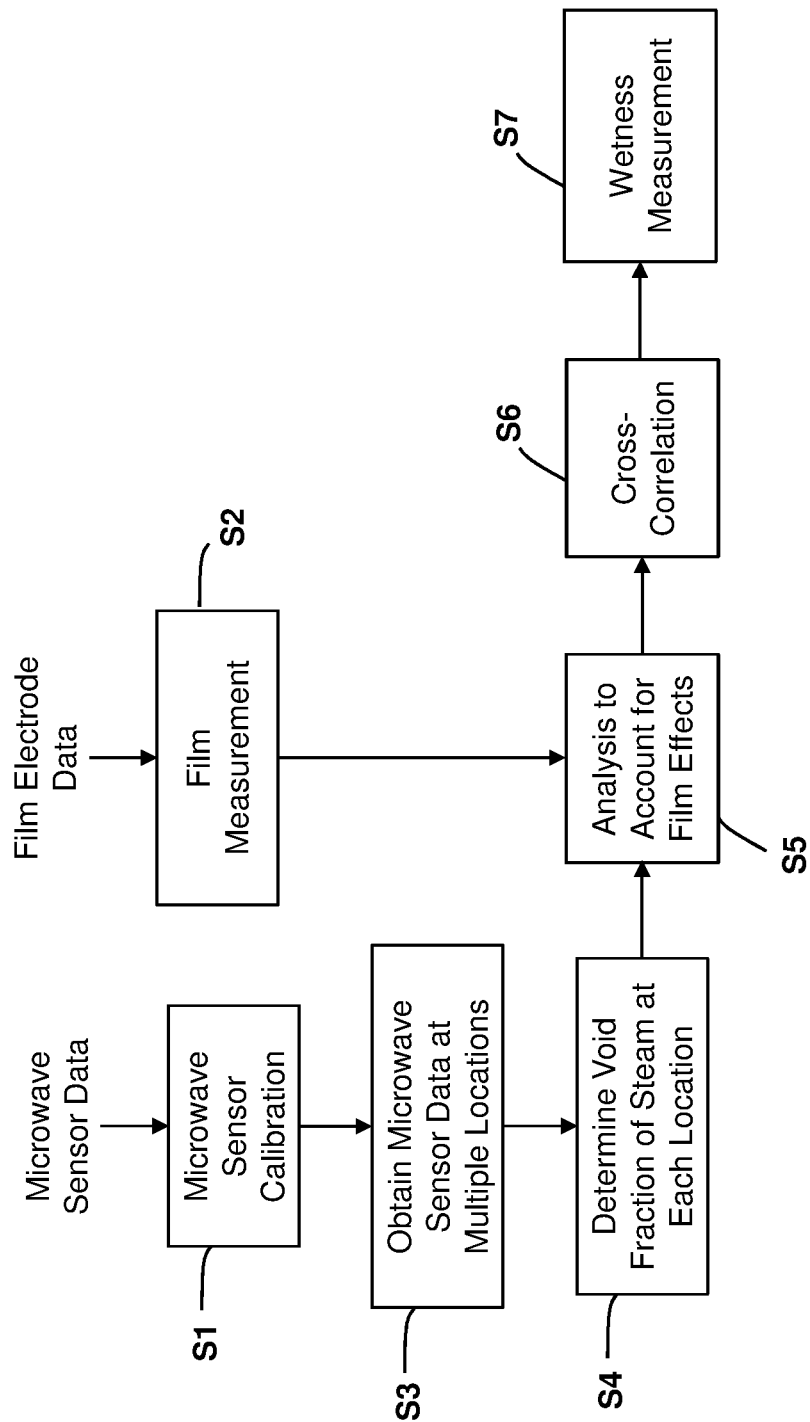
FIG. 5 depicts a process for microwave tomography steam wetness measurement according to various embodiments.

FIG. 5 depicts a process for microwave tomography steam wetness measurement according to various embodiments. At S1, the phase shift measurement device 122 receives sensor data from the plurality of sets 106 of microwave sensors 108 and, based on the received sensor data, calibrates the microwave sensors 108. At S2, based on film electrode data received from the set of electrodes 112, the film measurement system 122 determines the thickness and flow velocity of the film 110 in the pipe 102. S2 may be performed before, during, or after S1. At S3, microwave sensor data from the now calibrated microwave sensors 108 is obtained at a plurality of locations within the pipe 102 and, at S4, the microwave sensor data is analyzed to determine void fraction data of the steam 104 at each of the plurality of locations.

At S5, an analysis 128 is performed to determine the effect of the film 110 on the void fraction data to provide modified void fraction data. At S6, the modified void fraction data for the plurality of locations is cross-correlated 130, and a steam wetness measurement 132 of the steam 104 is determined at S7.

The microwave tomography steam wetness measurement system 100 provides high speed, real time, wet steam measurement, for application in pipework. The microwave tomography steam wetness measurement system 100 is suitable for retrofit and new builds.

In various embodiments, components described as being "coupled" to one another can be joined along one or more interfaces. In some embodiments, these interfaces can include junctions between distinct components, and in other cases, these interfaces can include a solidly and/or integrally formed interconnection. That is, in some cases, components that are "coupled" to one another can be simultaneously formed to define a single continuous member. However, in other embodiments, these coupled components can be formed as separate members and be subsequently joined through known processes (e.g., fastening, ultrasonic welding, bonding). Fluidly coupled refers to a coupling through which a fluid can flow.

When an element or layer is referred to as being "on", "engaged to", "connected to" or "coupled to" another element, it may be directly on, engaged, connected or coupled to the other element, or intervening elements may be present. In contrast, when an element is referred to as being "directly on," "directly engaged to", "directly connected to" or "directly coupled to" another element, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A system for measuring steam wetness, comprising:
    a plurality of microwave sensors for detecting microwave signals passing through a supply of steam flowing through a cavity;
    a film measurement system for measuring a characteristic of a film flowing along inner surface of the cavity;
    a system for determining a characteristic of the steam flowing through the cavity based on data provided by the plurality of microwave sensors;
    a system for determining a wetness of the steam flowing through the cavity based on the characteristic of the steam flowing through the cavity and the characteristic of the film flowing along the inner surface of the cavity; and
    a calibration system for calibrating the plurality of microwave sensors, the calibration system obtaining phase shift and attenuation measurements over a range of frequencies using the plurality of microwave sensors.

2. The system for measuring steam wetness according to claim 1, wherein the cavity comprises a pipe.

3. The system for measuring steam wetness according to claim 1, wherein the plurality of microwave sensors are distributed about a circumference of the cavity.

4. The system for measuring steam wetness according to claim 3, further comprising a plurality of sets of microwave sensors, wherein each set of microwave sensors is disposed at a different location along the cavity and obtains the microwave signals at that location.

5. The system for measuring steam wetness according to claim 4, wherein the system for determining the wetness of the steam flowing through the cavity determines the characteristic of the steam at each different location of the sets of microwave sensors along the cavity.

6. The system for measuring steam wetness according to claim 5, wherein the system for determining the wetness of the steam flowing through the cavity cross-correlates the characteristic of the steam determined at each different location.

7. The system for measuring steam wetness according to claim 1, wherein the characteristic of the film on the inner surface of the cavity comprises at least one of a thickness of the film and a flow velocity of the film.

8. The system for measuring steam wetness according to claim 1, wherein the characteristic of the steam flowing through the cavity comprises a void fraction of the steam.

9. The system for measuring steam wetness according to claim 1, further comprising a system for modifying the characteristic of the steam based on the determined characteristic of the film.

10. The system for measuring steam wetness according to claim 1, wherein the film measurement system comprises at least one electrode for detecting a conductivity of the film.

11. The system for measuring steam wetness according to claim 1, wherein the plurality of microwave transducers extend into an interior of the cavity beyond, and isolated from, the film.

12. A method for measuring steam wetness, comprising:
 detecting, using a plurality of microwave sensors, microwave signals passing through a supply of steam flowing through a pipe;
 measuring a characteristic of a film flowing along an inner surface of the pipe;
 determining a characteristic of the steam flowing through the pipe based on data provided by the plurality of microwave sensors;
 determining a wetness of the steam flowing through the pipe based on the characteristic of the steam flowing through the pipe and the characteristic of the film on the inner surface of the pipe; and
 calibrating the plurality of microwave sensors prior to the detecting, the calibrating including obtaining phase shift and attenuation measurements over a range of frequencies using the plurality of microwave sensors.

13. The method for measuring steam wetness according to claim 12, wherein the characteristic of the film comprises at least one of a thickness of the film and a flow velocity of the film.

14. The method for measuring steam wetness according to claim 12, wherein the characteristic of the steam flowing through the pipe comprises a void fraction of the steam.

15. The method for measuring steam wetness according to claim 12, wherein the plurality of microwave transducers extend into an interior of the pipe beyond, and isolated from, the film.

16. The method for measuring steam wetness according to claim 12, wherein the detecting further comprises detecting, at a plurality of different locations along the pipe, the microwave signals passing through the supply of steam flowing through the pipe, and wherein the determining the wetness of the steam flowing through the pipe further comprises cross-correlating the characteristic of the steam determined at each of the plurality of different locations.

17. The method for measuring steam wetness according to claim 16, further comprising modifying the characteristic of the steam based on the determined characteristic of the film.

18. A combined cycle power generation system, comprising:
 a gas turbine system;
 a steam turbine system powered by steam generated using exhaust gases from the gas turbine system; and
 a system for measuring a wetness of the steam, including:
  a plurality of microwave sensors for detecting microwave signals passing through a supply of steam flowing through a pipe;
  a calibration system for calibrating the plurality of microwave sensors;
  a film measurement system for measuring a characteristic of a film flowing along inner surface of the pipe;
  a system for determining a characteristic of the steam flowing through the pipe based on data provided by the plurality of microwave sensors;
 a system for determining a wetness of the steam flowing through the pipe based on the characteristic of the steam flowing through the pipe and the characteristic of the film flowing along the inner surface of the pipe; and
 a calibration system for calibrating the plurality of microwave sensors, the calibration system obtaining phase shift and attenuation measurements over a range of frequencies using the plurality of microwave sensors.

* * * * *